United States Patent [19]
Gunther

[11] Patent Number: 5,154,175
[45] Date of Patent: Oct. 13, 1992

[54] INTRAUTERINE FETAL EKG-OXIMETRY CABLE APPARATUS

[76] Inventor: Ted J. Gunther, c/o Dr. Shen-Gunther 98th General Hospital, Dept. OB-Gyn Box 76, Apo, N.Y. 09105

[21] Appl. No.: 663,688

[22] Filed: Mar. 4, 1991

[51] Int. Cl.[5] .............................................. A61B 5/02
[52] U.S. Cl. ................................. 128/633; 128/662.03
[58] Field of Search ............. 128/633, 661.08, 661.07, 128/662.03, 662.04, 665, 698, 778, 632, 662.06, 664

[56] References Cited

U.S. PATENT DOCUMENTS

| | | | |
|---|---|---|---|
| 4,173,221 | 11/1979 | McLaughlin et al. | 128/696 |
| 4,573,474 | 3/1986 | Scibetta | 128/644 |
| 4,807,631 | 2/1989 | Hersh et al. | 128/633 |

Primary Examiner—William E. Kamm
Assistant Examiner—Scott M. Getzow
Attorney, Agent, or Firm—Leon Gilden

[57] ABSTRACT

An apparatus including an organization to process signals regarding information to pulse rate and oxygen saturation of arterial blood flow in a fetus. The organization includes guide cable including sensors mounted to a housing, wherein the housing includes an adhesive plate, and the adhesive plate includes a central fetal scalp electrode directed orthogonally and outwardly relative to the fetal scalp between the first and second sensors. The first and second sensors are directed to provide information regarding oxygen saturation and pulse rate readings, while the fetal scalp electrode is directed to an EKG monitoring station.

4 Claims, 4 Drawing Sheets

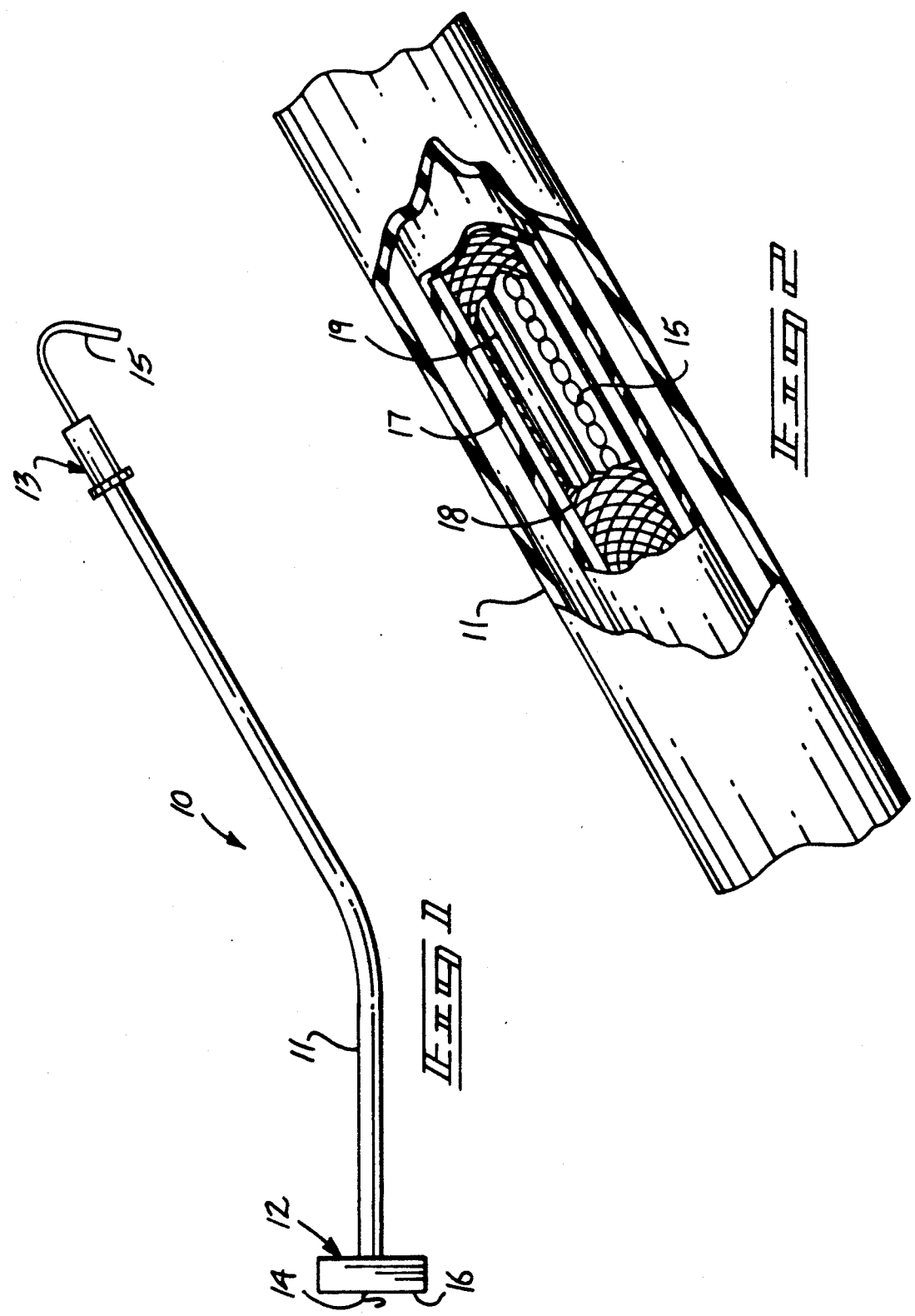

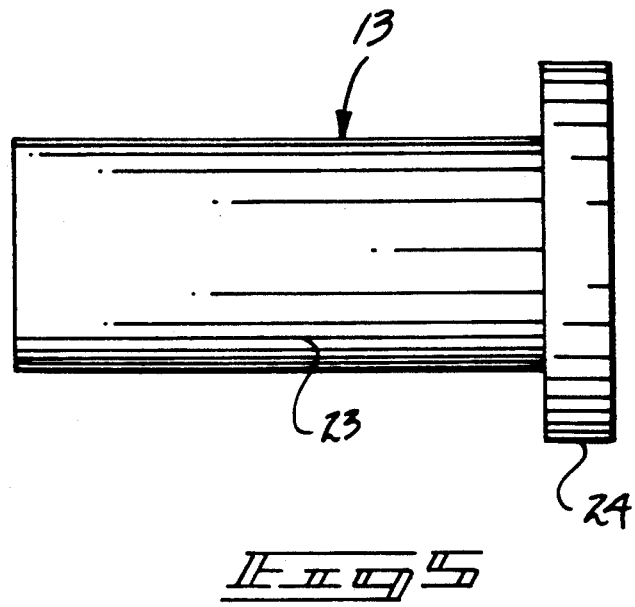
FIG 5
FIG 6
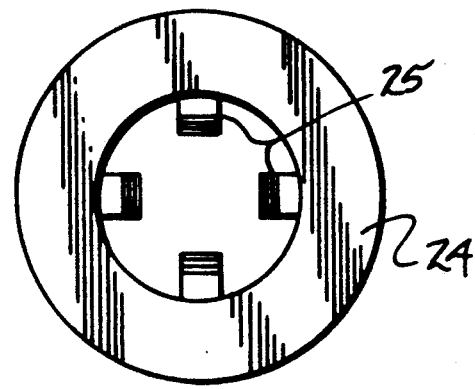

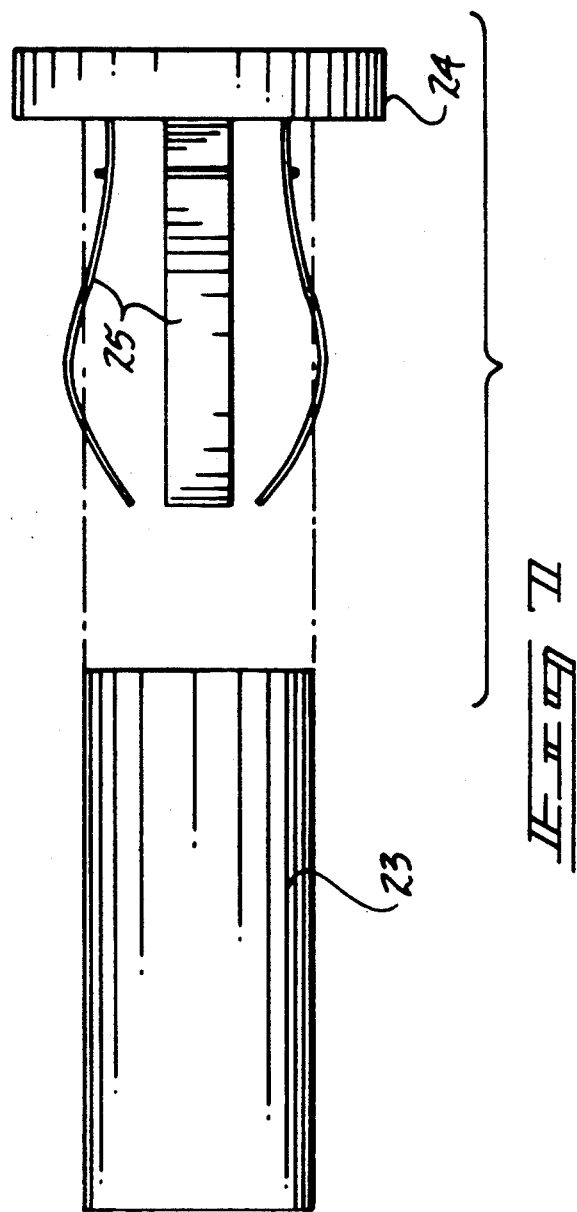

INTRAUTERINE FETAL EKG-OXIMETRY CABLE APPARATUS

BACKGROUND OF THE INVENTION

1. Field of the Invention

The field of invention relates to oximetry and signal processing techniques employed in oximetry and EKG monitoring.

2. Description of the Prior Art

Typical oximetry techniques, particularly as they relate to fetal monitoring, has heretofore failed to provide adequate information relating to EKG monitoring during the oximetry sensing procedure. Fetal heart rate organizations for adequate information in association with measurement of the pulsatile heart rate and oxygen saturation level utilized in conventional oximetry organizations has heretofore been attempted. Conventional oximetry apparatus and sensing may be found in U.S. Pat. No. 4,800,495 setting forth prior art oximetry signal generation and analysis.

Pulse transmitting oximetry essentially involves measurement to effect arterial blood in tissue relative to intensity of light passing therethrough. The blood in the tissue is directed as a function of arterial Pulse, with a greater volume available at systole pressure and a lesser volume available at diastole pressure. As blood absorbs light passing through the tissue, intensity of that light directed through the tissue is arranged in an inverse relationship relative to a volume of blood available in tissue at that simultaneous instance.

U.S. Pat. No. 4,807,631 to Hersh, et al. sets forth a further example of a pulse oximetry system, wherein U.S. Pat. Nos. 4,573,474 to Scibetta and 4,173,221 to McLaughlin, et al. are arranged for electro-cardiogram monitoring apparatus.

As such, it may be appreciated that there continues to be a need for a new and improved intrauterine fetal EKG-oximetry cable apparatus as set forth by the instant invention which addresses both the problems of ease of use as well as effectiveness in construction in presenting monitoring of a fetal heart rate through the measuring procedure of the pulsatile heart rate and oxygen saturation level

SUMMARY OF THE INVENTION

In view of the foregoing disadvantages inherent in the known types of oximetry apparatus now present in the prior art, the present invention provides an intrauterine fetal EKG-oximetry cable apparatus wherein the same is arranged for simultaneous monitoring of fetal heart rate directed through and simultaneous with measurement of the pulsatile heart rate and oxygen saturation level relative to an unborn infant. As such, the general purpose of the present invention, which will be described subsequently in greater detail, is to provide a new and improved intrauterine fetal EKG-oximetry cable apparatus which has all the advantages of the prior art oximetry apparatus and none of the disadvantages.

To attain this, the present invention provides an apparatus including an organization to process signals regarding information to pulse rate and oxygen saturation of arterial blood flow in a fetus. The organization includes guide cable including sensors mounted to a housing, wherein the housing includes an adhesive plate, and the adhesive plate includes a central fetal scalp electrode directed orthogonally and outwardly relative to the fetal scalp between the first and second sensors. The first and second sensors are directed to provide information regarding oxygen saturation and pulse rate readings, while the fetal scalp electrode is directed to an EKG monitoring station.

My invention resides not in any one of these features per se. but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the Present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the Public generally, and especially the scientists, engineers and practitioners in the art who are not familiar with Patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved intrauterine fetal EKG-oximetry cable apparatus which has all the advantages of the prior art oximetry apparatus and none of the disadvantages.

It is another object of the present invention to provide a new and improved intrauterine fetal EKG-oximetry cable apparatus which may be easily and efficiently manufactured and marketed.

It is a further object of the present invention to provide a new and improved intrauterine fetal EKG-oximetry cable apparatus which is of a durable and reliable construction.

An even further object of the present invention is to provide a new and improved intrauterine fetal EKG-oximetry cable apparatus which is susceptible of a low cost of manufacture with regard to both materials and labor, and which accordingly is then susceptible of low prices of sale to the consuming public, thereby making such intrauterine fetal EKG-oximetry cable apparatus economically available to the buying public.

Still yet another object of the present invention is to provide a new and improved intrauterine fetal EKG-oximetry cable apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the instant invention.

FIG. 2 is an orthographic side view, partially in section, of the cable structure of the instant invention.

FIG. 5 is an orthographic side view of the connector member utilized by the instant invention.

FIG. 6 is an orthographic end view of the connector member as illustrated in FIG. 5.

FIG. 7 is an orthographic side view, somewhat exploded, of the connector member as utilized by the instant invention.

DESCRIPTION OF THE PREFERRED EMBODIMENT

Figure 3:
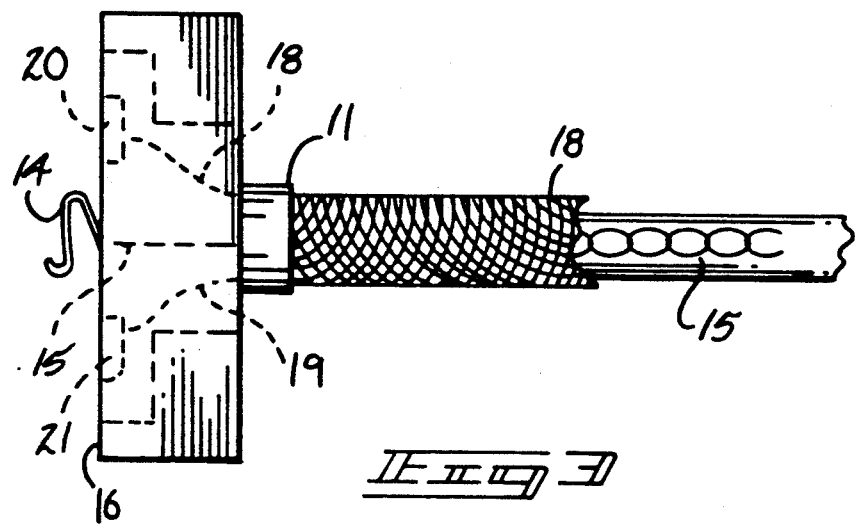
FIG. 3 is an orthographic enlarged side view of the cable and scalp mounting housing utilized by the instant invention.
Figure 4:
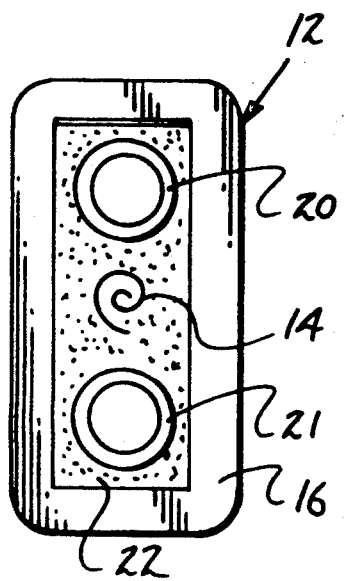
FIG. 4 is an orthographic front view of the housing as illustrated in FIG. 3.

With reference now to the drawings, and in particular to FIGS. 1 to 7 thereof, a new and improved intrauterine fetal EKG-oximetry cable apparatus embodying the principles and concepts of the present invention and generally designated by the reference numeral 10 will be described.

More specifically, the intrauterine fetal EKG-oximetry cable apparatus 10 of the instant invention essentially comprises an elongate uterine guide tube 11 formed of a flexible, polymeric impermeable material arranged for positioning within a uterus of a patient, with the guide tube including mounting housing 12 fixedly and orthogonally mounted to a first end of the guide tube, with the guide tube including a resilient elastomeric connector 13 mounted at the opposed second end of the guide tube arranged for securement to oximetry analysis equipment, in a manner as set forth in U.S. Pat. No. 4,800,495 incorporated herein by reference. The resilient elastomeric connector 13 includes an electrode delivery cable 15 extending exteriorly and medially through the connector 13 for mounting to conventional EKG equipment for monitoring fetal heart rate of a type as set forth in U.S. Pat. No. 4,173,221 incorporated herein by reference.

The housing 12 includes a planar housing forward face 16 orthogonally oriented relative to the guide tube 11 mounted to the rear face of the housing, with the forward face 16 including a respective first and second sensor 20 and 21 respectively, wherein the first sensor 20 utilizes a red optical filter in association with an LED sensor 21 arranged for monitoring the oxygen saturation level and pulse rate of a fetus. A fetal scalp electrode 14 of a spiral, coil configuration extends forwardly of and beyond the forward face 16 and is positioned medially between the first and second sensor 21, wherein the fetal scalp electrode 14 is arranged for penetration of the fetal scalp region permitting monitoring of the fetal heart rate. Accordingly, the fetal scalp electrode 14 is of a relatively rigid construction in electrical communication with the electrode delivery cable 15. A first communication cable 18 is in operative association with the first sensor 20 defined as a sheath, with the second communication cable 19 in communication with the second sensor 21 to direct information to the associated oximetry analyzing equipment.

An adhesive plate surface 22 is formed in contiguous relationship with the housing forward face 16 in surrounding relationship to the first and second sensors 20 and 21 respectively, as well as the fetal scalp electrode 14, for maintaining securement of the forward face 16 to a fetal scalp surface.

The elastomeric connector 13 includes a rigid alignment ring 24 mounting a tubular connector housing 23 thereto, wherein the electrode connectors 25 of a spring connection are arranged for securement to the aforenoted oximetry equipment, of a type as utilized and set forth in U.S. Pat. No. 4,800,495. It is to be understood that the cooperative relationship of the EKG and oximetry mounting of the organization sets forth an apparatus permitting a complete organization for setting forth complete information regarding understanding of physiological information of pulse rate, oxygen saturation, and coronary and vascular of an associated fetal patient.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be ted by Letters Patent of the United States is as follows:

1. An intrauterine fetal EKG-oximetry cable apparatus comprising, an elongate, flexible guide tube, the guide tube formed of an impermeable polymeric material, including a first end and a second end, the first end including a housing of a generally parallelepiped configuration fixedly and orthogonally mounted at the first end of the guide tube, the mounting housing mounting the first end at a rear face of the mounting housing, and the mounting housing including a forward face, with the forward face orthogonally oriented relative to connection of the guide tube at the rear face, and the forward face including a first red optical sensor cooperative with a second LED sensor directed through the forward face, and the first sensor and the second sensor including a respective first communication cable and second communication cable directed through the guide tube, and a resilient elastomeric connector mounted to the second end of the guide tube, with the resilient connector including the first communication cable and the second communication cable directed therethrough adapted for mounting to oximetry analyzing apparatus, and an adhesive plate surface contiguous with and mounted in surrounding relationship to the first sensor and the second sensor on the housing forward face.

2. An apparatus as set forth in claim 1 including a heart monitoring EKG cable directed through the guide tube and extending exteriorly of the second end of the guide tube adapted for securement to an EKG monitoring system, wherein the EKG cable is directed through the guide tube into the housing.

3. An apparatus as set forth in claim 2 including a fetal scalp electrode positioned medially of the first sensor and second sensor, with the fetal scalp electrode directed orthogonally of and extending exteriorly of the forward face.

4. An apparatus as set forth in claim 3 wherein the fetal scalp electrode includes a spiral, coil configuration adapted for securement within a fetus for monitoring fetal heart rate.

* * * * *